(12) United States Patent
Atzinger et al.

(10) Patent No.: US 7,142,632 B2
(45) Date of Patent: Nov. 28, 2006

(54) RADIATION IMAGE RECORDING DEVICE

(75) Inventors: Franz Atzinger, Nürnberg (DE); Roland Herrmann, Marktredwitz (DE); Volkmar Köhler, Röttenbach (DE); Helmuth Schramm, Neunkirchen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/527,434

(22) PCT Filed: Sep. 22, 2003

(86) PCT No.: PCT/DE03/03138

§ 371 (c)(1), (2), (4) Date: Mar. 10, 2005

(87) PCT Pub. No.: WO2004/028368

PCT Pub. Date: Apr. 8, 2004

(65) Prior Publication Data

US 2005/0279942 A1    Dec. 22, 2005

(30) Foreign Application Priority Data

Sep. 25, 2002   (DE) ............................ 102 44 609

(51) Int. Cl.
*G01N 23/06* (2006.01)
(52) U.S. Cl. .................................. 378/62; 378/196
(58) Field of Classification Search .................. 378/21, 378/22, 24–27, 189, 98.12, 62, 55, 196
See application file for complete search history.

(56) References Cited

U.S. PATENT DOCUMENTS

| | | | |
|---|---|---|---|
| 5,631,942 A | * | 5/1997 | Shinoda .................. 378/98.12 |
| RE36,162 E | * | 3/1999 | Bisek et al. ................. 378/146 |
| 6,078,699 A | | 6/2000 | Lobregt et al. |
| 6,081,582 A | * | 6/2000 | Mazess et al. .............. 378/146 |
| 6,097,833 A | * | 8/2000 | Lobregt et al. ............. 382/130 |
| 6,222,906 B1 | * | 4/2001 | Sakaguchi et al. ......... 378/98.8 |
| 6,282,264 B1 | * | 8/2001 | Smith et al. ................. 378/189 |
| 6,851,851 B1 | * | 2/2005 | Smith et al. ................. 378/189 |
| 2002/0018589 A1 | | 2/2002 | Beuker et al. |

FOREIGN PATENT DOCUMENTS

| | | |
|---|---|---|
| DE | 42 31 583 A1 | 3/1994 |
| DE | 101 34 651 A1 | 2/2003 |
| EP | 1 223 751 A1 | 7/2002 |

* cited by examiner

*Primary Examiner*—Edward J. Glick
*Assistant Examiner*—Hoon Song

(57) ABSTRACT

Disclosed is a radiation image recording device comprising a source of radiation and a radiation receiver which are movable in a vertical direction in order to be positioned relative to a standing patient, and an image processing device for creating an output image based on the recorded image data. The source of radiation and the radiation receiver are movable in a controlled manner into successive image recording positions via a control device so as to record an area of analysis which exceeds the height of the active area of the digital radiation receiver, one radiation image being recorded in each image recording position. The positions are defined in such a way that the recorded radiation images cover the area of analysis while the image processing device is embodied so as to create a full image representing the entire area of analysis based on the image data of the individual radiation images.

18 Claims, 2 Drawing Sheets

RADIATION IMAGE RECORDING DEVICE

CROSS REFERENCE TO RELATED APPLICATIONS

This application claims priority to the German application No. 10244609.1, filed Sep. 25, 2002 and to the International Application No. PCT/DE03/03138, filed Sep. 22, 2003 which are incorporated by reference herein in their entirety.

FIELD OF INVENTION

The invention relates to a radiation imaging device with a radiation source and a radiation receiver, which can be moved in a vertical direction to be positioned in relation to a standing patient, and with an image processing device for producing an image that can be output based on the recorded image data.

BACKGROUND OF INVENTION

In modern X-ray-based diagnostics it is increasingly frequently necessary to examine large examination areas, e.g. the entire spinal column or the leg area to diagnose bone positions. The patient is hereby scanned in a standing position with the radiation imaging device, i.e. a conventional X-ray device comprising an X-ray tube and an X-ray radiation receiver. The receiver generally has a 40×120 cm film cassette, if this is large enough to map the whole examination area. As an alternative it is known that smaller film cassettes can be used to record a plurality of storage plate images, which map the examination area, and these can then be stuck together to give an overall image. This process is elaborate and complex and the storage plates require subsequent development, which takes a relatively long time, so diagnosis can not take place at the same time as recording.

DE 42 31 583 A1 discloses an angiographic X-ray diagnostics device, with which a plurality of individual images are produced of a prone patient by incremental displacement. The individual images are stored in an image storage unit of a laser image reproduction device, display lines being omitted from the edges of the images so that an image of the entire examination area can be printed out on the laser image reproduction device without overlap.

SUMMARY OF INVENTION

An object of the invention is therefore to specify an improved radiation imaging device.

To achieve this object according to the invention, with a radiation image recording of the type mentioned above comprising a digital radiation receiver, i.e. a known semiconductor flat detector, to record an examination area exceeding the height of the active area of the radiation receiver, the radiation source and radiation receiver can be moved in a controlled manner into successive imaging positions by means of a control device, a radiation image being recorded in each of these positions, the positions being defined such that the recorded radiation images cover the examination area and the image processing device being configured to produce an overall image representing the entire examination area based on the image data of the individual radiation images.

The invention advantageously proposes incremental scanning of the examination area, a radiation image being recorded in every defined imaging position. A central control device controls the radiation source and radiation receiver into the respectively defined position and once the image has been recorded, it is read from the radiation receiver and sent to the image processing device. When the entire examination area has been scanned by recording a plurality of images, the overall image representing the entire examination area is produced by computation in the image processing device based on the data of the individual radiation images. This overall image can then be output and the diagnosis made.

Compared with the prior art the radiation imaging device according to the invention has a number of advantages. On the one hand the overall image is produced very quickly, as, if its design is adequate, the image processing device can compute the overall image immediately after the last individual image is produced. Diagnosis can therefore take place almost immediately after the last individual image has been recorded. Also the image processing device advantageously produces a single overall image, which can be output immediately after its production. There is therefore no longer any need for complex or time-consuming development or for the additional process of sticking individual images together after development. A further important advantage is that this overall image can be archived without further ado in a suitable patient data management unit, which can be achieved in a significantly simpler manner by storage on a suitable data medium than the hitherto standard archiving of storage plate images.

A further important advantage is that the device used to implement the recording technique defined above can be a standard thorax or skeleton recording device, which does not have to be modified very much for this purpose, except primarily in respect of the image processing device, which must be designed accordingly.

Generally the radiation imaging device according to the invention allows the fast and uncomplicated and immediately informative production of an overall image of a large examination area, which is significantly larger than the active area of the radiation receiver.

In a development of the invention, the control device can be configured for the automatic determination of the respective positions based on the height of the examination area and the height of the active area of the radiation detector. Before the image is actually recorded, the doctor therefore determines which examination area is to be scanned. In the example the left leg is to be examined from the heel to the neck of the femur. The doctor inputs said patient parameters into the control device, which then uses the known active area of the radiation detector, i.e. the detector area used actively for imaging, where X-ray radiation is converted to image data, to compute the position to which the radiation source and radiation receiver must automatically be moved. This procedure is possible both when the active area of the radiation detector is not variable and with detectors with a variable active area, i.e. with which the doctor can select a specific detector range, to use for the actual imaging process. As set out above, this area is known to the control device, as is therefore the height of the area in relation to the vertical movement, so that the relevant recording positions can be automatically determined and automatically assumed without further ado.

The radiation source and radiation receiver are thereby expediently moved synchronously, i.e. they are moved from one position to the next at the same time. Of course operation with asynchronous movement is also required, with first one and then the other component being moved. Movement always takes place symmetrically, i.e. always by the same distance, so that with the type of recording, in which a standing patient is scanned, the radiation source and radiation receiver are always opposite each other in a horizontal plane, thus they are always in the same plane.

Movement from one recording position to the next and imaging in the respective recording position advantageously take place automatically. Therefore when imaging starts, once the individual recording positions have been determined, the control device moves the radiation source and radiation receiver, which is for example as 40×40 cm image receiver, from an initial position, to which both components are always moved as the basic position, to the first recording position. When this has been done imaging takes place automatically and when the recorded individual image has been read, both are moved to the next recording position, where recording again takes place, etc. This process continues until the last image has been recorded, whereupon both components are for example moved back to the initial position. In parallel with this the image processing device immediately starts to process the individual image data to produce the overall image. This also expediently takes place automatically, so that after activating the start button the doctor really has nothing more to do until the final image is output.

As described, the image processing device is configured such that it uses the individual images to produce an overall image that shows the entire examination area precisely mapped and with exact resolution for diagnostic purposes. It must also be able to position two adjacent images of the examination area in relation to each other and join them such that there are no edges or misalignments and the examination area, e.g. the lower leg, is mapped precisely in respect of the recorded structure. To this end it is expedient according to a first embodiment of the invention for the positions in which the recordings are made to be defined such that two successively recorded images overlap at the edges. Therefore two successively recorded images show the same structures at the edges, on the basis of which the image processing device, e.g. using suitable edge detection algorithms or similar algorithms, which detect the commonalities in the images, can determine the precise alignment of the two images in respect of each other and superimpose them exactly. Of course this is done so that no edges, brightness differences, etc. caused by the superimposition are visible in the overall image produced. The superimposition should thereby not be too large; a superimposition of for example 3–5 cm is possible based on a 40×40 cm image receiver. Sufficient structural commonalities are already present in such a relatively narrow area to allow exact alignment and overlapping of both images on the part of the image processing device.

In an alternative embodiment of the invention the positions are defined such that two successively recorded images are essentially adjacent to each other. The overlap here is therefore only a few millimeters. Production of the overall image here depends primarily on the one hand on the fact that the radiation source and radiation receiver can be moved exactly into the predefined positions and on the other hand that the patient does not move during the process. Both images are almost directly adjacent to each other. Here too of course the imaging processing device can carry out an analysis of the edge area in respect of corresponding structures, in so far as some occur in the few millimeters of overlap. As an alternative to analyzing the two edge areas, it is also possible to use suitable algorithms to search for continuing structures in the first and second images. While for example the edges of a bone are detected in the first recorded image, these edges are also determined in the next recorded image and both images are positioned in respect of each other such that the edges coincide or are precise continuations of each other.

The overall image can either be exposed onto a film if necessary in a reduced format as a hard copy, e.g. written onto a storage plate, or can be output on a monitor. Outputting on a monitor is of course essential for fast diagnosis. The overall image can thereby be output on the monitor in the recorded format or in a larger format. As the monitor is of course smaller than the recorded examination area, the clearly larger overall image is viewed simply by moving the overall image on the monitor, which can be done by scrolling. It is if course also possible to display the overall image in an enlarged format compared with the actual recorded format, so that some structures can be displayed even larger.

The radiation source and radiation receiver are expediently arranged on, if necessary telescopic, ceiling or floor gantries, which allow simple automatic movement. A suitable mechanical system is provided for this purpose, which in particular allows exact positioning of both components in the respectively defined recording position, in order to be able to record the individual images, as defined beforehand by means of the control device.

For structural reasons the radiation receiver, i.e. the solid state detector, in particular cannot be moved to just above the floor, i.e. the active area is always a certain distance above the ground. For leg imaging it is however necessary for the heel bone at least to be mapped. To resolve this, according to the invention a platform is provided to hold the patient with retaining devices for the patient. This platform, on which the patient has to stand, compensates for this misalignment due to the structure, so that the heel bone is also recorded without further ado. The retaining devices are provided so that the patient stands firm and without movement, as said patient cannot change position while the plurality of individual images are being recorded.

The retaining devices can thereby be configured as handles, the height of which can be varied, so that people of differing heights can be secured optimally. It is also possible to design the retaining means as corresponding straps, etc., which are used to belt the patient firmly in position.

A radiation-transparent plate is also expediently provided on the platform on the side facing the radiation receiver, to prevent the patient coming into contact with the radiation receiver.

BRIEF DESCRIPTION OF THE DRAWINGS

Further advantages, features and details of the invention will emerge from the exemplary embodiment described below and with reference to the drawings, in which.

DETAILED DESCRIPTION OF INVENTION

Figure 1:
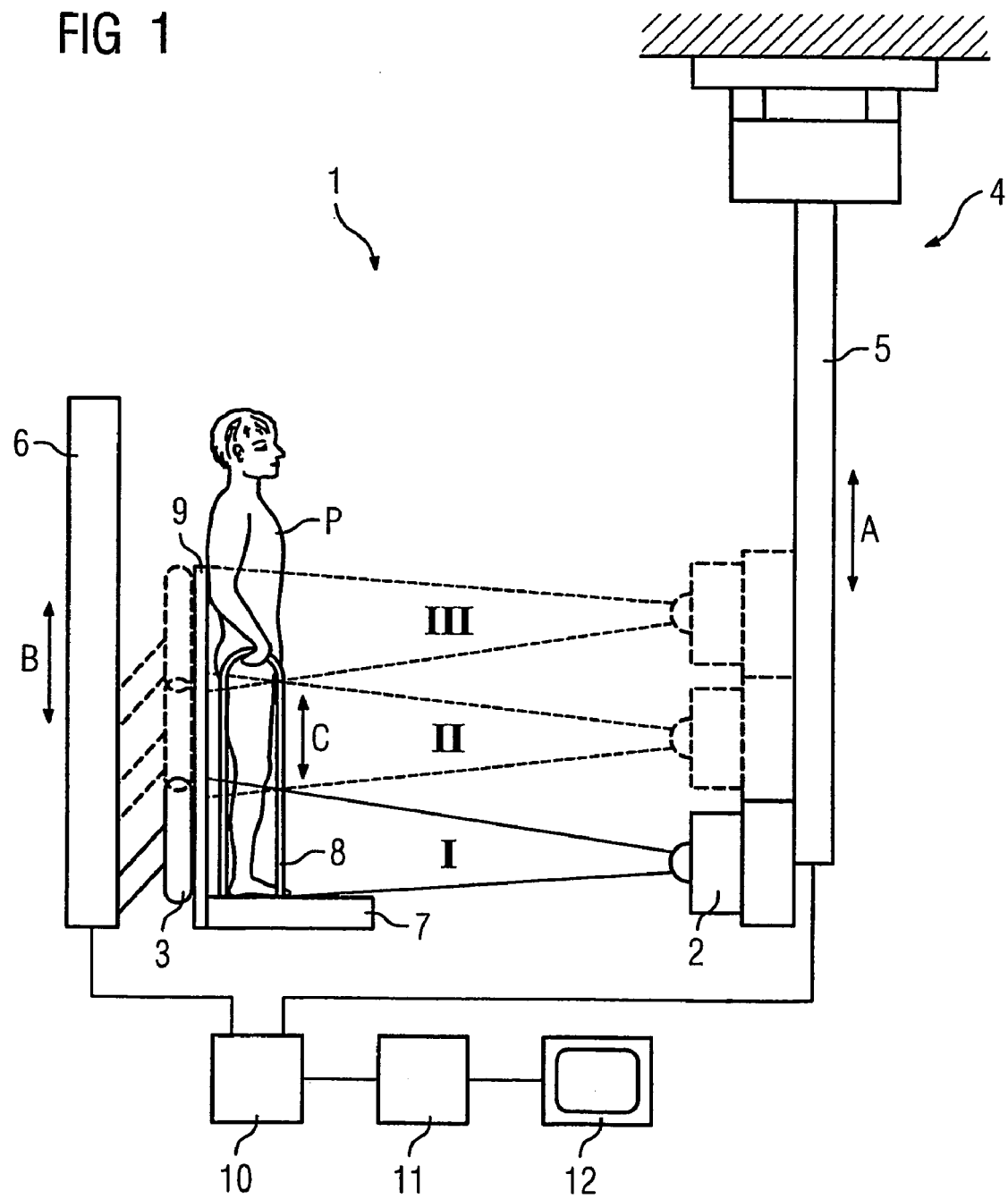
FIG. 1 shows a schematic sketch of a radiation imaging device according to the invention.

FIG. 1 shows a radiation imaging device 1 according to the invention, comprising a radiation source 2, in this case an X-ray emitter, and a radiation receiver 3, in this case a digital solid state detector. The radiation source 2 is arranged on a gantry 4 with a telescopic bar 5 and can therefore be moved vertically as shown by the double arrow A. The same applies to the radiation receiver 3. This is also arranged on a gantry 6 and can also be moved vertically, as shown by the double arrow B. While the gantry 4 is supported on the ceiling, the gantry 6 is a floor gantry.

A platform 7 is provided in the vicinity of the radiation receiver, on which the patient P has to stand for the recording. Retaining means 8 in the form of vertically movable handles (see double arrow C) are arranged on both sides of the platform 7, which the patient can hold on to, as said patient has to stand still during imaging. A radiation-transparent plate 9 is also provided at the back, arranged there for protection purposes to prevent the patient coming into contact with the radiation receiver 3.

The radiation imaging device according to the invention also comprises a central control device 10, to which an imaging processing device 11 and a monitor 12 are assigned. The control device 10 is used to control the vertical displacement of the radiation source 2 and the radiation receiver 3 exactly so that different recording positions can be assumed and to control the imaging operation. The image processing device 11 is used to compute an overall image from the recorded individual images, which is then recorded on the monitor 12.

In the exemplary embodiment shown the right leg of the patient P is to be recorded and output as an overall image for the doctor. To this end, the doctor uses a suitable input means (e.g. a keyboard, etc. not shown in more detail here) to input the geometric data of the examination area, in this case the right leg, into the control device 10. The doctor must define the extent of the examination area in relation to the vertical. In this instance the examination area is clearly larger than the active area of the radiation receiver 3. To be able to map it exactly in an overall image, it is necessary to produce a plurality of individual images in different recording positions, in order to be able to compute an overall image therefrom. When the vertical position and length of the examination area have been defined, the control device 10 computes the positions to which the radiation source 2 and radiation receiver 3 must be moved, in order to record individual images of the examination area, which map this as a whole. This can be done by the control device 10 without further ado, as it knows the examination area exactly and is able to locate it based on the corresponding data input by the doctor and it also knows the active area of the radiation receiver 3, i.e. the area in which the image data mapping the examination area is actually generated. The respective recording positions, into which the radiation source 2 and radiation receiver 3 have to be moved to image the examination area, can be determined from these without further ado. In the exemplary embodiment shown there are three recording positions. Starting from the lowest recording position I, to which the control device moves the radiation source and radiation receiver, from an initial position (not shown), a first image is recorded there, showing the leg of the patient from the heel bone to below the knee for example. After successful recording, which is also controlled via the control device 10, the image data of this first image is read out and sent to the image processing device 11. The radiation source 2 and radiation receiver 3 are then moved to the recording position II, the positions being determined exactly in each instance using suitable position detection means. Once they arrive there, a second individual image is recorded, showing the leg of the patient below the knee to the center of the thigh. After successful recording and reading of the image data, a third movement takes place to the third recording position III, where a third image is recorded on arrival, showing the examination area from the center of the thigh to the hip. When this image has been recorded, it too is read out and sent to the image processing device 11, in which there are then three individual images. These three individual images are then used to produce an overall image by computation, which is then output on the monitor 12.

The recording positions are thereby defined such that for example two successively recorded individual images overlap by a certain distance. Based on an approx. 40×40 cm image receiver, the active area of which is therefore 40×40 cm for example, the overlap can be 3 or 5 cm for example. This is expedient so that the image processing device 11 can use suitable algorithms to detect coincident areas in two successively recorded images and can thus position the images exactly in relation to each other, to give a uniform overall image without edges and brightness differences, etc. Alternatively the recording positions can also be selected so that the images connect together almost seamlessly, the image processing device 11 then using suitable algorithms to search for continuing structures in two successively recorded images, in order to be able to align both images in relation to each other.

In each case the entire operation is carried out automatically via the control device 10. If said control device 10 knows the parameters mentioned above relating to the examination area, the recording positions are determined automatically depending on which image processing mode (i.e. with edge overlap or directly adjacent) has been selected, by the doctor for example. Once this is all defined, the doctor only has to press the start button on the control device 10, whereupon the entire imaging, displacement and image evaluation process operates automatically.

As an alternative to inputting any parameters relating to the examination area, it is of course also possible for the doctor to define the examination area by moving the radiation detector to a first position and a second position, which approximately define the positions for the first and last recorded images. The examination area is thus as if defined directly in the coordinates system of the movement tracking system of the radiation receiver. Based on these two positions, the respective intermediate recording positions can then be determined. It is thereby possible of course that the overall length of the examination area is not precisely a multiple of the height of the active area of the receiver, taking into account any overlaps. It is therefore possible for this purpose to use corresponding diaphragms at the radiation source during the last recording just to radiate a sub-area, etc. Thus different variations are possible for defining the position and length of the examination area.

Figure 2:
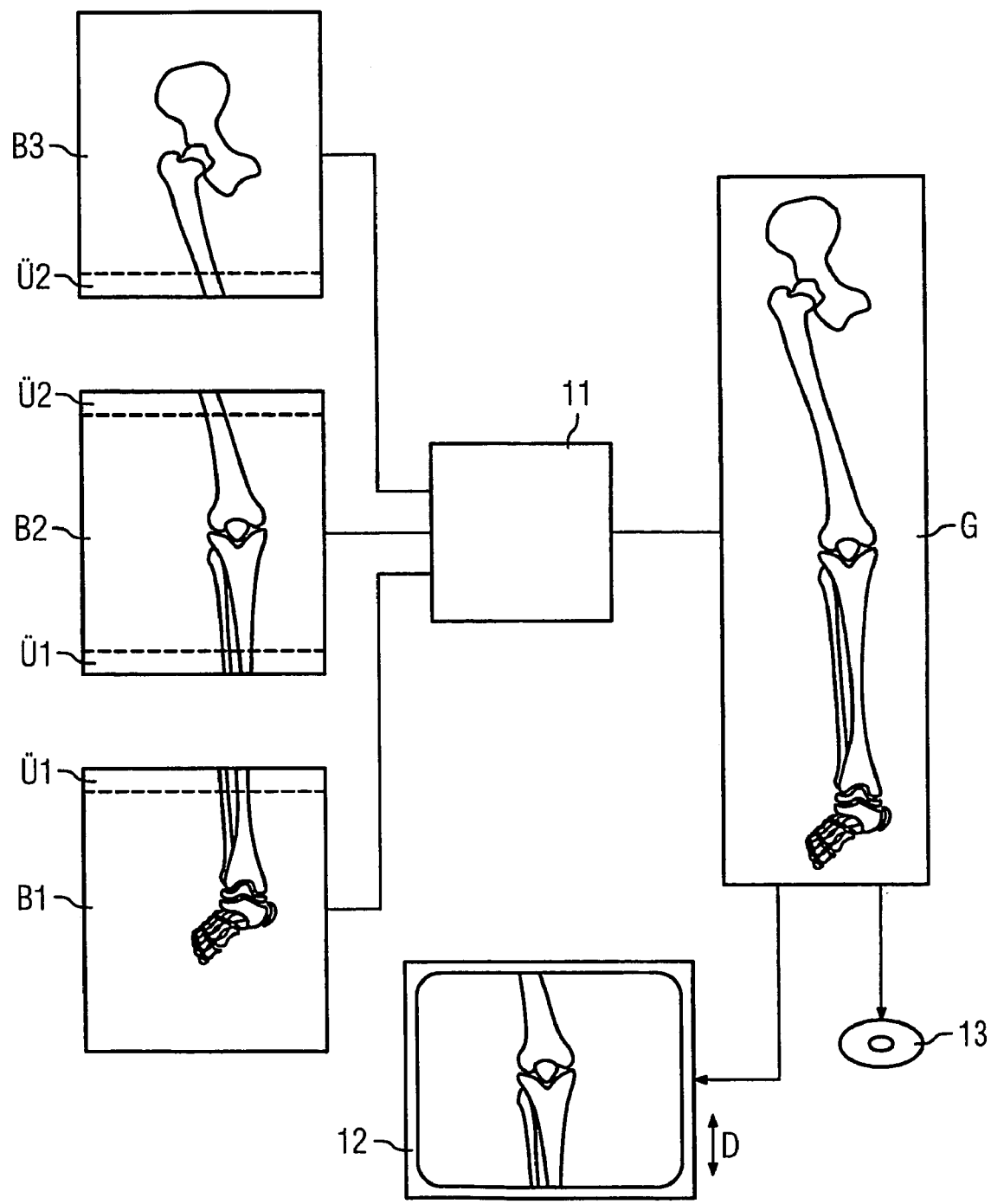
FIG. 2 shows a schematic sketch showing the "fusion" of three individual images to produce an overall image.

FIG. 2 is in the form of a schematic sketch showing how three individual images are used to produce an overall image. In the example shown three individual images B1, B2 and B3 were recorded.

The individual image B1 was recorded first, showing the majority of the lower leg to just below the knee. The individual image B2 is then recorded, showing the knee and some of the thigh. Finally the individual image B3 is recorded, showing the remainder of the thigh with the neck of the femur.

For simple arrangement of the images in relation to each other, the images were recorded so that they overlap partially. Each image contains an area of overlap with the previously recorded image, in other words an area in which the recorded structure is coincident to this extent. In the image B1 this is the upper narrow edge area Ü1. Individual image B2 also has the area of overlap Ü1 at its lower edge with an area of overlap Ü2 at its upper edge, which is repeated in the same way in the next recorded individual image B3. The imaging processing device 11 is now able to use these areas of overlap to align two successive images exactly in respect of each other using suitable analysis algorithms and overlap these in the region of the areas of overlap, thus producing an overall image G, which shows the entire examination area from the foot to the neck of the femur. Image fusion is thereby such that there are no edges or brightness differences, etc. in the region of the transitions from one individual image to another.

The overall image thus produced is now expediently output on the monitor 12. As the image area of said monitor is smaller than the overall image G, which expediently shows the examination area 1:1, only part of the overall image G can be displayed on the monitor 12. A suitable scrolling device can now be used to move the image on the monitor 12 without further ado, as shown by the double arrow D.

As well as displaying the digital overall image B on the monitor, it is also possible without further ado to archive said image and store it on a data medium, in the example shown here a CD-ROM 13. Given the enormous amount of storage space on such a data medium, a plurality of further overall images can of course also be stored there (as can individual images of course), thereby allowing significantly more expedient and convenient archiving than when the storage plates used in the prior art had to be stored.

The invention claimed is:

1. A medical imaging device, comprising:
   a radiation source;
   a digital radiation detector for recording images, the radiation source and the digital radiation detector configured to be moved vertically relative to a patient in a standing position;
   a control device adapted to move the radiation source and the digital radiation detector to a plurality of successive imaging positions for recording an image of an examination area having a height exceeding a height of an active surface area of the digital radiation detector; and
   an image processing device for generating a combined image showing the examination area, wherein
   the plurality of successive imaging positions are calculated by the control device based on user input data providing the height of the examination area and based on the height of the active surface area of the digital radiation detector,
   an image is recorded at each imaging position, the images recorded at the imaging positions in their entirety covering the examination area, and
   the image processing device is configured to generate the combined image using the images recorded at the imaging positions.

2. The medical imaging device according to claim 1, wherein the control device is adapted to move the radiation source and the digital radiation detector synchronously.

3. The medical imaging device according to claim 1, wherein the control device is further adapted to move the radiation source and the digital radiation detector to the imaging positions successively using an automation program.

4. The medical imaging device according to claims 1, wherein the images recorded at adjacent imaging positions overlap in an overlap area.

5. The medical imaging device according to claim 1, wherein the images recorded at adjacent imaging positions overlap a few millimeters at edge areas of the respective adjacent images.

6. The medical imaging device according to claim 4, wherein the imaging processing device is further adapted to arrange the images recorded at the adjacent imaging positions relative to the combined image using the overlap area.

7. The medical imaging device according to claim 5, wherein the imaging processing device is further adapted to arrange the images recorded at the adjacent imaging positions relative to the combined image using algorithms to search for continuing structures in the respective adjacent images and to position the respective adjacent images in respect of each other such that edges of the continuing structures in the respective adjacent images coincide or are precise continuations of each other.

8. The medical imaging device according to claims 1, wherein the combined image is displayed on a monitor or printed on a hardcopy.

9. The medical imaging device according to claim 8, wherein the displayed or printed combined image is scaled down.

10. The medical imaging device according to claim 1, wherein the combined image is displayed on a monitor using a display format corresponding to a recording format of the combined image, the combined image movable on the monitor using a scrolling mechanism.

11. The medical imaging device according to claim 1, wherein the combined image is displayed on a monitor using a display format exceeding the original size of the examination area, the combined image movable on the monitor using a scrolling mechanism.

12. The medical imaging device according to claim 1, wherein the radiation source and the digital radiation detector are arranged on adjustable wall- or floor-mounted supports.

13. The medical imaging device according to claim 12, wherein the supports are telescopic supports.

14. The medical imaging device according to claim 1, further comprising a platform for accommodating the patient, the platform having a safeguard device for securing the patient's standing position.

15. The medical imaging device according to claim 14, wherein the safeguard device includes a handhold.

16. The medical imaging device according to claim 14, further comprising a plate permeable for radiation emitted by the radiation source, the plate arranged on the platform and facing the digital radiation detector.

17. The medical imaging device according to claim 1, wherein the user input data is provided by input means to input the geometric data, including the height, of the examination area.

18. The medical imaging device according to claim 1, wherein the user input data is provided by movement of the radiation detector to a first position and to a second position to define a first and a last image of the plurality of successive imaging positions.

* * * * *